(12) United States Patent
Ohlbach et al.

(10) Patent No.: US 6,683,180 B2
(45) Date of Patent: Jan. 27, 2004

(54) METHOD FOR THE PRODUCTION OF CAPROLACTAM

(75) Inventors: Frank Ohlbach, Dossenheim (DE); Andreas Ansmann, Wiesloch (DE); Rolf-Hartmuth Fischer, Heidelberg (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/297,209

(22) PCT Filed: Jun. 13, 2001

(86) PCT No.: PCT/EP01/06687

§ 371 (c)(1),
(2), (4) Date: Dec. 4, 2002

(87) PCT Pub. No.: WO01/96294

PCT Pub. Date: Dec. 20, 2001

(65) Prior Publication Data

US 2003/0153749 A1 Aug. 14, 2003

(30) Foreign Application Priority Data

Jun. 16, 2000 (DE) .......................................... 100 28 950

(51) Int. Cl.$^7$ ............................................ C07D 201/08
(52) U.S. Cl. .................................................... 540/539
(58) Field of Search ........................................ 540/539

(56) References Cited

U.S. PATENT DOCUMENTS 4,119,665 A   10/1978   Weitz et al. ............ 260/561 A
6,331,624 B1 * 12/2001   Koch et al. .................. 540/538

FOREIGN PATENT DOCUMENTS

| DE | 915 568 | 7/1954 |
|---|---|---|
| EP | 023 751 | 2/1981 |
| EP | 576 976 | 1/1994 |
| GB | 2 108 119 | 5/1983 |
| WO | WO 97/30973 | * 8/1997 |

OTHER PUBLICATIONS

Polymer letters, vol. 2, 491–493 (1964).
JP 5330/55 (1955).

* cited by examiner

*Primary Examiner*—Bruck Kifle
(74) *Attorney, Agent, or Firm*—Keil & Weinkauf

(57) ABSTRACT

A process is provided for the preparation of caprolactam from a compound of formula (I):

$$NC-(CH_2)_5-CO-R \qquad (I)$$

in which R is a carboxamide, carboxylic acid or carboxylic acid ester group,
wherein a) a compound (I) or a mixture of such compounds, in the presence of ammonia and optionally a liquid diluent (VI), is hydrogenated with hydrogen in the presence of a catalyst (II) to give a mixture (III), b) the hydrogen and the catalyst (II) are separated from the mixture (III) to give a mixture (IV), and c) the mixture (IV), optionally in the presence of a liquid diluent (VII), is converted to caprolactam in the presence of a catalyst (V).

9 Claims, No Drawings

METHOD FOR THE PRODUCTION OF CAPROLACTAM

The present invention relates to a process for the preparation of caprolactam from a compound of formula (I):

$$NC-(CH_2)_5-CO-R \quad (I)$$

in which R is amino, hydroxyl or alkoxy,
wherein
a) a compound (I) or a mixture of such compounds, in the presence of ammonia and optionally a liquid diluent (VI), is hydrogenated with hydrogen in the presence of a catalyst (II) to give a mixture (III),
b) the hydrogen and the catalyst (II) are separated from the mixture (III) to give a mixture (IV), and
c) the mixture (IV), optionally in the presence of a liquid diluent (VII), is converted to caprolactam in the presence of a catalyst (V).

Processes for the preparation of caprolactam from compounds of formula (I) are known per se.

Thus DP 915 568 describes the conversion of cyanovaleric acid esters on Raney cobalt at 120° C. and 200 bar to give caprolactam yields of 40–52%.

The conversion of cyanovaleric acid esters on Raney catalysts is also described in J. Polym. Sci. Part B, Polymer Lett. 2 (1964) no. 5, pages 491–3. Caprolactam yields of 31–74% are obtained.

EP-A-23 751 describes the hydrogenation of cyanovaleric acid esters on Ru/Fe fixed bed catalysts to give caprolactam yields of 35%.

According to JP 305330, cyanovaleric acid esters are first hydrogenated on Raney nickel or Raney cobalt and then thermolyzed without a catalyst to give caprolactam yields of 80–90%.

The disadvantage of these processes is that the yields or space-time yields are too low to meet industrial demands.

It is an object of the present invention to provide a process which makes it possible to prepare caprolactam from compounds of formula (I) in a technically simple and economic manner, avoiding said disadvantages.

We have found that this object is achieved by the process defined at the outset.

According to the invention, the compound (I) used has the formula

$$NC-(CH_2)_5-CO-R \quad (I)$$

in which R amino, hydroxyl or alkoxy.

It is also possible to use mixtures of such compounds, these also being referred to as the compound (I) in terms of the present invention. It is particularly preferred to use a single compound as the compound (I).

Suitable carboxamide groups are advantageously those of the general formula $-CO-NR^1R^2$, in which $R^1$ and $R^2$ independently of one another are hydrogen or an organic radical, preferably $C_1-C_4$ alkyl. The particularly preferred carboxamide group is the group $-CONH_2$.

Suitable carboxylic acid ester groups are advantageously those of the general formula $-CO-OR^3$, in which $R^3$ is an organic radical, preferably $C_1-C_4$ alkyl. The particularly preferred carboxylic acid ester group is the group $-CO-OCH_3$.

The preparation of compounds of formula (I) is generally known, for example from Reppe, Lieb. Ann. Chem. 596 (1955) 127, BE 850 113, EP-A-576976 or EP-A-1 107 947.

According to the invention, in step a), the compound (I), in the presence of ammonia and optionally a liquid diluent (VI), is hydrogenated with hydrogen in the presence of a catalyst (II) to give a mixture (III).

Advantageously, at least 0.1 kg, preferably 0.1 to 10 kg, particularly preferably 0.2 to 5 kg and very particularly preferably 0.5 to 5 kg of ammonia should generally be used per kg of compound (I).

Step a) can advantageously be carried out in the presence of a liquid diluent (VI). Suitable diluents (VI) are preferably water or organic diluents, for example $C_4$ to $C_9$ alkanols such as n-butanol, i-butanol or n-pentanol, ethers such as methyl tert-butyl ether or tetrahydrofuran, preferably aliphatic hydrocarbons such as n-hexane, cycloaliphatic hydrocarbons such as cyclopentane or cyclohexane, and especially aromatic hydrocarbons such as benzene, toluene, o-xylene, m-xylene, p-xylene, ethylbenzene, i-propylbenzene or di-i-propylbenzene, as well as mixtures of such compounds, for example petroleum ethers. The hydrocarbons can carry functional groups such as halogens, for example chlorine, as in chlorobenzene.

A suitable catalyst (II) is advantageously a heterogeneous catalyst, said catalyst (II) preferably being used as a fixed bed catalyst. A metal selected from the group consisting of Fe, Ni, Co and Ru, or mixtures thereof, is useful as the catalytically active component of the catalyst (II).

Such components can be used as an unsupported catalyst, for example as Raney nickel, Raney cobalt or iron obtained by reduction from synthetic or natural materials containing iron oxide, for example magnetite.

Such components can be used as a supported catalyst. Suitable supported catalysts can advantageously be obtained by impregnating or spraying a support with a solution containing compounds of such metals or mixtures thereof, or by spray drying a suspension containing a support and compounds of such metals or mixtures thereof. Such supported catalysts can contain supports known per se, preferably aluminum oxide, silicon oxide, aluminosilicates, lanthanum oxide, titanium dioxide, zirconium dioxide, magnesium oxide, zinc oxide, zeolites or activated carbon, or mixtures thereof.

In step a), the proportion of compound (I), based on the sum of the starting components, namely compound (I), ammonia and diluent (VI), is advantageously 0.1 to 50% by weight, preferably 1 to 30% by weight and particularly preferably 2 to 20% by weight.

The reaction can advantageously be carried out in the liquid phase.

The reaction can advantageously be carried out at temperatures generally of 40 to 250° C., preferably of 50 to 100° C. and particularly preferably of 60 to 120° C. The pressure should generally range from 1 to 350 bar, preferably from 25 to 250 bar.

The reaction of step a) yields a mixture (III).

In step b), the hydrogen and the catalyst (II) are separated from the mixture (III) to give a mixture (IV).

The catalyst (II) can be separated off in a manner known per se.

In the case of a suspension procedure, the catalyst (II) can advantageously be separated off by filtration, especially through a membrane of appropriate pore size. In the case of a fixed bed procedure, the reaction mixture can advantageously be withdrawn from the reactor to leave the catalyst (II) in the reactor.

The hydrogen can be separated off in a manner known per se, preferably in a high pressure separator. The high pressure separator can advantageously be followed by [text missing] for separating off any remaining hydrogen.

All or part of the ammonia can advantageously be separated off in step b).

The separation can advantageously be carried out by distillation, especially at bottom temperatures of 60 to 220° C. and pressures of 1 to 30 bar.

A mixture (IV) is obtained after step b).

According to the invention, in step c), a mixture (IV), optionally in the presence of a liquid diluent (VII), is converted to caprolactam in the presence of a catalyst (V).

Step c) can advantageously be carried out in the presence of a liquid diluent (VII). Suitable diluents (VII) are preferably water or organic diluents, for example $C_1$ to $C_9$ alkanols such as methanol, ethanol, n-propanol, isopropanol, n-butanol, i-butanol or n-pentanol, preferably aliphatic hydrocarbons such as n-hexane, cycloaliphatic hydrocarbons such as cyclopentane or cyclohexane, and especially aromatic hydrocarbons such as benzene, toluene, o-xylene, m-xylene, p-xylene, ethylbenzene, i-propylbenzene or di-i-propylbenzene, as well as mixtures of such compounds, for example petroleum ethers. The hydrocarbons can carry functional groups such as halogens, for example chlorine, as in chlorobenzene.

Advantageously, the diluents (VI) and the diluents (VII) can be identical.

A suitable catalyst (V) is advantageously a heterogeneous catalyst. The catalyst (V) can preferably be used as a fixed bed catalyst.

Suitable catalysts (V) are acidic, basic or amphoteric oxides of the elements of main group II, III or IV of the periodic table, such as calcium oxide, magnesium oxide, boron oxide, aluminum oxide, tin oxide or silicon dioxide in the form of pyrogenic silicon dioxide, silica gel, kieselguhr, quartz or mixtures thereof, and also oxides of metals of subgroups II to VI of the periodic table, such as amorphous titanium dioxide in the form of anatase or rutile, zirconium dioxide, manganese-oxide or mixtures thereof. It is also possible to use lanthanide and actinide oxides such as cerium oxide, thorium oxide, praseodymium oxide, samarium oxide, a rare earth mixed oxide or mixtures thereof with the abovementioned oxides. Examples of other possible catalysts are:

vanadium oxide, barium oxide, zinc oxide, niobium oxide, iron oxide, chromium oxide, molybdenum oxide, tungsten oxide or mixtures thereof. Mixtures of said oxides with one another are also possible. Some sulfides, selenides and tellurides, such as zinc telluride, tin selenide, molybdenum sulfide, tungsten sulfide and the sulfides of nickel, zinc and chromium, can also be used.

The abovementioned compounds can be doped with, or contain, compounds of main groups I and VII of the periodic table.

Other suitable catalysts which may be mentioned are zeolites, phosphates and heteropolyacids, as well as acidic and alkaline ion exchangers like Nafion.

Preferred catalysts are titanium oxide, aluminum oxide, cerium oxide and zirconium dioxide, particularly preferred catalysts being activated aluminum oxides such as those disclosed e.g. by In the reaction of step c), ammonia can also be present, but is preferably absent.

In step c), the proportion of the compound formed from the compound (I) in step a) (compound (VIII)), based on the sum of this compound (VIII) and the diluent (VII), is advantageously 0.1 to 50% by weight, preferably 1 to 30% by weight and particularly preferably 2 to 20% by weight.

The reaction can advantageously be carried out in the liquid phase at temperatures generally of 140 to 320° C., preferably of 180 to 300° C. and particularly preferably of 200 to 280° C. The pressure should generally range from 1 to 250 bar, preferably from 5 to 150 bar.

The preferred pressure and temperature conditions here are those under which the reaction mixture is in the form of a single homogeneous liquid phase.

The catalyst loadings generally range from 0.05 to 5, preferably from 0.1 to 2 and particularly preferably from 0.2 to 1 kg of compound (VIII) per 1 catalyst volume per hour.

The reaction of step c) yields a mixture containing caprolactam. In addition to caprolactam, this mixture generally contains low-boiling components, high-boiling components, compound (VIII), optionally ammonia and diluent (VII).

In terms of the present invention, low-boiling components are understood as meaning compounds boiling below caprolactam and high-boiling components are understood as meaning compounds boiling above caprolactam.

Caprolactam can be obtained from this mixture by methods known per se, such as extraction or distillation. In the case of distillation, the work-up can advantageously be effected by fractional distillation in one or more, such as 2 or 3, distillation apparatuses.

Suitable apparatuses are those conventionally used for distillation, for example those described in: Kirk-Othmer, Encyclopedia of Chemical Technology, 3rd ed., vol. 7, John Wiley & Sons, New York, 1979, pages 870–881, such as sieve-plate columns, bubble-cap columns or packed columns.

Preferably, any ammonia and diluent (VII) still present are appropriately separated from the mixture first. The high-boiling components, the low-boiling components and any unreacted compound (VIII) can then be separated from the remaining mixture, individually or together, to give caprolactam.

Advantageously, all or part of the diluent (VII) obtained in this work-up can be recycled into step a) or step c).

Advantageously, all or part of any high-boiling and/or low-boiling components obtained in this work-up can be recycled into step c).

Advantageously, all or part of any unreacted compound (VIII) obtained in this work-up can be recycled into step c).

The caprolactam obtained in the process according to the invention can be used in a manner known per se for the preparation of industrially important polymers such as polyamides.

EXAMPLES a) Batch Hydrogenation of Methyl Cyanovalerate

Methyl cyanovalerate, solvent and ammonia as the liquid phase were placed, as shown in table 1, in a 0.27 liter autoclave fitted with a wire basket insert containing 80 g of catalyst pellets, and with a gas injection stirrer, and were reacted under the conditions given in said table. The appropriate reaction pressure was kept constant by the continuous metering of hydrogen.

The results are shown in table 1.

TABLE 1

| Catalyst | Educts [g] | | | Reaction conditions | | | Product yield in [%] | | |
|---|---|---|---|---|---|---|---|---|---|
| | MCV | SOLV (79 g) | NH$_3$ | T [° C.] | p [bar] | t [min] | MAH | AH | CL |
| Magnetite | 8.8 | MTBE | 8.1 | 110 | 250 | 30 | 92.4 | 3.0 | 3.6 |
| Magnetite | 17 | toluene | 8.1 | 110 | 250 | 35 | 96.7 | 1.8 | 1.6 |
| Raney Ni | 17 | — | 69 | 50 | 100 | 220 | 91.0 | 5.9 | 0.3 |
| Cobalt | 17 | — | 69 | 90 | 250 | 30 | 93.8 | 3.7 | 0.9 |
| Cobalt | 17 | — | 69 | 50 | 100 | 70 | 98.2 | 0.8 | 0.3 |
| Cobalt | 8.8 | toluene | 69 | 50 | 100 | 165 | 93.9 | — | 1.1 |
| Cobalt | 8.8 | toluene | 8.1 | 50 | 100 | 160 | 94.0 | 0.6 | 1.2 |
| Raney Co | 17 | — | 69 | 50 | 100 | 45 | 91.7 | 1.1 | 1.1 |
| Raney Co | 8.8 | toluene | — | 50 | 100 | 65 | 93.6 | — | 0.3 |
| Hydro—talcite | 8.8 | toluene | 8.1 | 50 | 100 | 22 | 90.5 | 3.9 | 3.4 |
| Raney Co | 8.8 | toluene | 8.8 | 60 | 100 | 90 | 98.1 | 1.0 | 0.6 |
| Raney Co | 8.8 | toluene | 19.6 | 60 | 100 | 90 | 98.8 | 0.8 | 0.3 |

MCV: methyl 6-cyanovalerate
MAH: methyl 6-aminohexanoate
AH: 6-aminohexanamide
CL: caprolactam
MTBE: methyl t-butyl ether b) Batch Cyclization of Methyl 6-Aminohexanoate to Caprolactam 2 ml (1.6 g) of a 10% by weight solution of methyl 6-aminohexanoate in toluene were converted, as shown in table 2, in a 5 ml autoclave at 150° C., with or without 1 g of powdered catalyst.

The conversions of methyl 6-aminohexanoate to caprolactam in [%] are shown in table 2.

TABLE 2

| | Catalyst | | | | | | |
|---|---|---|---|---|---|---|---|
| t [min] | none | SiO$_2$ | prec. Al$_2$O$_3$ | TiO$_2$ | ZrO$_2$ | MgO | CaO |
| 15 | 4.4 | 46.9 | 70.3 | 53.1 | 43.7 | 8.1 | 4.7 |
| 30 | 5.2 | 69.7 | 89.1 | 73.6 | 63.1 | 11.6 | 5.8 |
| 45 | 5.9 | 80.0 | 92.4 | 81.2 | 71.5 | 14.5 | 6.2 |
| 60 | 7.0 | 83.1 | 94.2 | 84.5 | 76.7 | 17.7 | 7.7 |
| 120 | 11.6 | 98.7 | 99.0 | 98.0 | 98.0 | 28.6 | 13.0 | c) Continuous Hydrogenation of Methyl Cyanovalerate
1. On a cobalt catalyst

In a 100 ml tubular reactor with a separate feed for educt solution, ammonia and hydrogen, 100 ml of cobalt catalyst were activated at 280° C. and the loading (in g MCV/ml catalyst/hour) and temperature were varied as shown in table 3 at a pressure of 200 bar and an ammonia/MCV ratio of 1:1.

The results are shown in table 3.

TABLE 3

| Loading | T [° C.] | MCV conversion [%] | MAH selectivity [%] |
|---|---|---|---|
| 0.3 | 80 | 94.60 | 94.46 |
| 0.15 | 80 | 98.64 | 98.63 |
| 0.2 | 80 | 95.31 | 95.31 |
| 0.2 | 90 | 98.46 | 98.08 |
| 0.2 | 100 | 99.36 | 99.04 |
| 0.2 | 120 | 99.92 | 99.32 |

MCV: methyl 6-cyanovalerate
MAH: methyl 6-aminohexanoate

2. On a Raney Cobalt Doped with Cr

In a 100 ml tubular reactor with a separate feed for educt solution, ammonia and hydrogen, and containing 100 ml of Cr-doped Raney Co, the loading (in g MCV/ml catalyst/hour) was varied as shown in table 4 at a pressure of 80 bar, a temperature of 80° C. and an ammonia/MCV ratio of 2:1.

The results are shown in table 4.

TABLE 4

| Loading | MCV conversion [%] | MAH selectivity [%] |
|---|---|---|
| 0.5 | 64.80 | 64.77 |
| 0.4 | 80.30 | 80.30 |
| 0.3 | 89.50 | 89.50 |
| 0.25 | 98.50 | 98.61 |
| 0.2 | 99.60 | 99.56 |

MCV: methyl 6-cyanovalerate
MAH: methyl 6-aminohexanoate d) Continuous Cyclization of Methyl 6-aminohexanoate to Caprolactam
1. On a TiO$_2$ Catalyst A 10% by weight solution of methyl 6-aminohexanoate in toluene, possibly containing water as shown in table 5, was converted on a TiO$_2$ catalyst (1.5 mm pellets) in a 20 ml tubular reactor (length 90 cm, diameter 6 mm) at the reaction temperature and loading (in 5 kg/l/h) shown in table 5.

The results are shown in table 5.

TABLE 5

| Loading | T [° C.] | Water [% by weight] | MAH conversion [%] | CL selectivity [%] |
|---|---|---|---|---|
| 0.5 | 200 | 0 | 95.44 | 94.54 |
| 0.4 | 200 | 0 | 97.73 | 95.24 |
| 0.5 | 220 | 0 | 98.30 | 96.85 |
| 0.5 | 220 | 0 | 98.64 | 96.23 |
| 0.5 | 220 | 5 | 98.93 | 96.44 |
| 0.5 | 250 | 0 | 97.56 | 94.95 |
| 0.5 | 240 | 0 | 96.87 | 95.85 |

TABLE 5-continued

| Loading | T [° C.] | Water [% by weight] | MAH conversion [%] | CL selectivity [%] |
|---|---|---|---|---|
| 0.5 | 230 | 0 | 97.42 | 97.31 |
| 0.5 | 220 | 0 | 97.92 | 96.58 |

MAH: methyl 6-aminohexanoate
CL: caprolactam

2. On a Gamma-Aluminum Oxide Catalyst

A 10% by weight solution of methyl 6-aminohexanoate in toluene, possibly containing water as shown in table 5, was converted on a gamma-aluminum oxide catalyst (1–3 mm chips) in a 20 ml tubular reactor (length 90 cm, diameter 6 mm) at the reaction temperature and loading (in kg/l/h) shown in table 6.

The results are shown in table 6.

TABLE 6

| Loading | T [° C.] | Water [% by weight] | MAH conversion [%] | CL selectivity [%] |
|---|---|---|---|---|
| 0.5 | 220 | 0 | 97.86 | 96.36 |
| 0.55 | 220 | 0 | 97.87 | 95.84 |
| 0.6 | 220 | 0 | 98.04 | 96.49 |

MAH: methyl 6-aminohexanoate
CL: caprolactam

We claim:

1. A process for the preparation of caprolactam from a compound of formula (I):

NC—(CH$_2$)$_5$—CO—R     (I)

in which R is an amino, hydroxy or alkoxy group, wherein a) a compound (I) or a mixture of such compounds, in the presence of ammonia and optionally a liquid diluent (VI), is hydrogenated with hydrogen in the presence of a catalyst (II) to give a mixture (III), b) the hydrogen and the catalyst (II) are separated from the mixture (III) to give a mixture (IV), and c) the mixture (IV), optionally in the presence of an aromatic hydrocarbon as a liquid diluent (VII), is converted to caprolactam in the presence of a catalyst (V).

2. The process of claim 1 wherein the catalyst (II) is a heterogeneous catalyst.

3. The process of claim 1 wherein the catalyst (II) is a fixed bed catalyst.

4. The process of claim 1 wherein the reaction mixture used in step a) is in liquid form during the hydrogenation.

5. The process of claim 1 wherein all or part of the ammonia is additionally separated off in step b).

6. The process of claim 1 wherein the catalyst (V) contains a metal oxide as the catalytically active component.

7. The process of claim 1 wherein the catalyst (V) is a fixed bed catalyst.

8. The process of claim 1 wherein a metal oxide selected from the group comprising titanium dioxide, aluminum oxide, cerium oxide and zirconium oxide, or mixtures thereof, is used as the catalytically active component of the catalyst (V).

9. The process of claim 1 wherein the diluent (VI) and the diluent (VII) are identical.

* * * * *